United States Patent [19]

Piccardi et al.

[11] 4,087,489
[45] May 2, 1978

[54] INSECTICIDAL N-POLYCHLOROALLYLAMIDO-THIO-PHOSPHORIC ESTERS

[75] Inventors: Paolo Piccardi; Francesco Corda, both of Milan; Franco Gozzo, Saronno (Varese); Angelo Longoni; Giovanni Renis, both of Milan, all of Italy

[73] Assignee: Montedison S.p.A., Milan, Italy

[21] Appl. No.: 680,694

[22] Filed: Apr. 27, 1976

[30] Foreign Application Priority Data

May 2, 1975 Italy ............................ 22948 A/75

[51] Int. Cl.$^2$ .......................... A01N 9/36; C07F 9/24
[52] U.S. Cl. .................................. 260/949; 260/954; 260/956; 424/216; 424/218; 424/219
[58] Field of Search ................... 260/956, 949, 954

[56] References Cited

U.S. PATENT DOCUMENTS

| 2,862,018 | 11/1958 | Kauer ............................... 260/956 |
| 2,892,751 | 6/1959 | Saul ................................ 260/956 |
| 3,880,960 | 4/1975 | Sirrenberg et al. ............... 260/956 |

Primary Examiner—Anton H. Sutto
Attorney, Agent, or Firm—Morgan, Finnegan, Pine, Foley and Lee

[57] ABSTRACT

The present invention concerns N-polychloroallylamidothiophosphoric esters. More particularly, this invention relates to new N-polychloroallylamido-thiophosphoric esters, the method for the preparation of same and their application in the fight against noxious insects.

6 Claims, No Drawings

INSECTICIDAL N-POLYCHLOROALLYLAMIDO-THIOPHOSPHORIC ESTERS

BACKGROUND OF INVENTION

Many phosphoric esters are known for their insecticide action. One of the best known is O,O-diethyl-O-p-nitrophenyl-phosphorthioate, described in German Pat. No. 814,152 and in U.S. Pat. Nos. 1,893,018 and 2,482,083, known on the market by the trade name of Parathion:

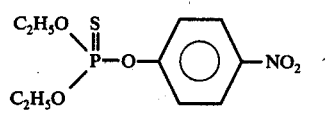

Notwithstanding its great effectiveness as an insecticide, the use of this compound meets with considerable difficulties due to its extreme toxicity for mammiferous animals.

In the class of aryl-phosphor-amidothioates derivatives, less studied than the previous compound, there is known the Zytron or DMPA; O-(2,4-dichlorophenyl)-O-methyl-N-isopropyl-phosphoro-amidothioate of the formula:

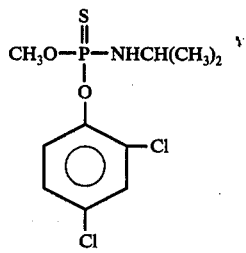

used as a herbicide or weed killer and marketed by the American Dow Chemical Company.

From a search carried out by some authors on similar O-methyl-O-(2,4,5-trichlorophenyl)-phosphoroamidothioates exerting an insecticidal action on flies, it was found that, while a further substitution with Cl on the benzene nucleus does not lead to any appreciable improvement, a lengthening or increase in molecular weight of the alkyl chain linked to the nitrogen atom causes a lowering of the biological activity against the "*Musca domestica*" (house fly) (see E. H. Blair et al: in 'Agricultural and Food Chemistry' 11 No. 3 (1963) page 237).

Thus, an object of this invention is that of describing a new class of phosphoric esters endowed with a high insecticide activity and having a relatively low toxicity for warm-blooded animals. Still another object is that of describing their method of preparation.

Still another object of this invention is that of describing the method for fighting infestations by noxious insects based on the use of such phosphoric esters.

GENERAL DESCRIPTION OF THE INVENTION

These and other objects still are obtained with the N-polychloroallylamido-thiophosphoric esters of this invention having the following general formula:

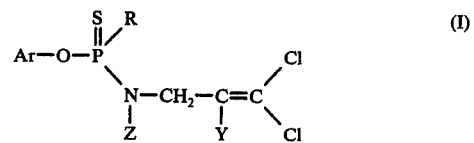

wherein:
- Ar = substituted phenyl
- R = $CH_3O$; $C_2H_5O$; iso-$C_3H_7O$; phenyl and substituted phenyl
- Z = H; $CH_3$; $C_2H_5$;

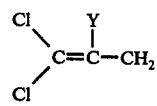

Y = H; Cl

More particularly, Ar may be 2,4,5-trichlorophenyl; 2,5-dichloro-4-bromophenyl; 2,5-dichloro-4-iodophenyl; 2,4-dichlorophenyl; 4-nitrophenyl; 3-methyl-4-nitrophenyl; 3-methyl-4-methylthiophenyl.

The process for the preparation of amido-thiophosphoric esters of general formula I is carried out starting from known intermediates. In general, one esterifies an O-aryl-phosphorodichloride according to the reaction:

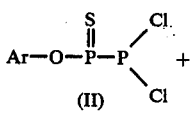

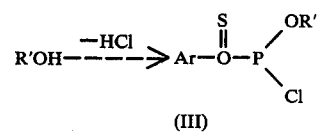

(wherein R' is a low alkyl).

One method of preparing the compounds of this invention is to react intermediate III with amine IV, according to the reaction:

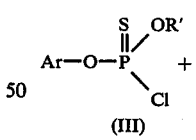

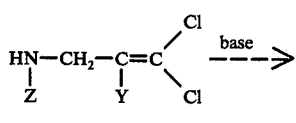

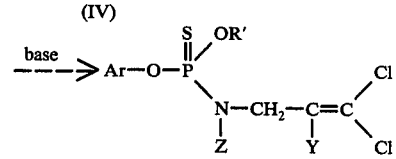

(Z and Y have the same meaning as that indicated in formula I).

Another method of preparing the compounds of this invention is that instead of the base as described in the above first method, there may be used a mol of

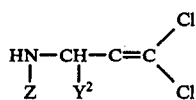

amine, that is, by reacting ester III with 2 mols of amine.

The terms of general formula I, wherein R = phenyl, are prepared by using the same sequence of reactions starting from the arylphosphorothiodichloride intermediate prepared by reacting PCl₃ with benzene in the presence of AlCl₃ according to the method of B. Buchner and L. B. Lokhart (Jour. Am. Chemical Society 73 – 1951, page 755) and by then adding sulphur to the phenyldichlorophosphine thus obtained.

The compounds of the invention have been proven to be active against various groups of insects: diptera, aphides, coleoptera.

Their action unfolds when spreading the active principle either as such or in the form of powdery mixtures with inerts, or in suspension or dispersion or in solution, on the habitat of the insect or on its nourishment or on the insect itself.

The acute toxicity in the albino mouse given oral doses (DL 50), for the compound of Example 1, has been proven to be greater than 100 mg/kg (in comparison Parathion has a D.L. 50 = 14 mg/Kg).

The excellent insecticidal activity shown by the compounds of this invention appears so much the more surprising when one considers that — as indicated at the beginning — in O-methyl-O-(2,4,5-trichlorophenyl)-phosphoro-amidothioates, an increase in the molecular weight of the alkyl chain bound to the nitrogen atom leads to a decrease in the biological activity towards the "*Musca domestica.*"

Even though the increase in molecular weight of the alkyl chain caused by the dichlorovinyl group bound to the nitrogen turns out to be quite considerable, the activity on the "*Musca domestica*" is excellent, as will appear from the following Table I:

TABLE I

Activity of "*Musca domestica*" by O-methyl-O-(2,4,5-trichlorophenyl)-phosphoroamidothioates with relationship to the weight of the alkyl group bound to the nitrogen atom (iso-C₃H₇ = 1) in comparison with that of the compound of Example 1 of this invention (in a quantity of 0.5 γ/insect):

| Compound | Relative weight of alkyl bound to nitrogen | Percentual death-rate on "*Musca domestica*" |
|---|---|---|
| CH₃O—P(=S)(O-phenyl-Cl)—NH—CH(CH₃)₂ (Zytron)* | 1 | 100 |
| CH₃O—P(=S)(O-2,4,5-trichlorophenyl)—NH—isoC₃H₇ | 1 | 100 |
| CH₃O—P(=S)(O-2,4,5-trichlorophenyl)—NH—(isoC₄H₉) | 1,32 | 92 |
| CH₃O—P(=S)(O-2,4,5-trichlorophenyl)—NH—(terC₄H₉) | 1.32 | 13 |

-continued

| Compound | Relative weight of alkyl bound to nitrogen | Percentual death-rate on "Musca domestica" |
|---|---|---|
| $C_2H_5-O-\overset{\overset{S}{\|}}{\underset{\underset{O}{\|}}{P}}-NH-CH_2-C=C\underset{Cl}{\overset{Cl}{\diagup}}$ with O-phenyl bearing Cl, Cl substituents | 2.56 | 100 | compare with example 1)
*compare Agricultural and Food Chemistry 11, no.3.(1963),p.237.

The compounds of this invention, when tested on plants for fighting insect infestation, are not phytotoxic.

SPECIFIC DESCRIPTION OF THE INVENTION

In order to better illustrate this invention, the following Examples will be given in the following.

EXAMPLE No. 1

Preparation of O-ethyl-O-(2,4,5-trichlorophenyl)-N-(3,3-dichloro-allyl)amido-thiophosphate.

Thirty-three grams (g) of O-(2,4,5-trichlorophenyl)-dichloro-thiophosphate (abt. 0.1 mol) dissolved in 33 cc of anhydrous ethyl ether were reacted with an excess of absolute ethyl alcohol (33 cc) in the presence of 9.2 g of triethylamine (0.99 mols), maintaining the temperature at 35° C by means of a heat stabilizing system, and under stirring. After 2 hours there were admixed 50 cc of anhydrous ethyl ether and the triethylamine hydrochloride was separated (12 g) by filtering.

The filtrate was then concentrated to a small volume and washed with a 2% aqueous solution of NaOH and then with water until reaching neutrality. The anhydrified organic phase was subjected to distillation, gathering the fraction boiling between 125° and 130° C at a pressure of 0.08 mm Hg. Thereby were obtained 14.2 g of O-ethyl-O-(2,4,5-trichlorophenyl) chlorothiophosphate (titre abt. 70%; 0.03 mols) which were reacted in ethyl ether (50 cc) with 4 g of 3,3-dichloroallylamine 0.03 moles dissolved in 50 cc of ethyl ether in the presence of 3.3 g of triethylamine (0.03 mols). The solution was maintained under stirring at 30° C for 10 hours.

At the end, by filtering, the triethylamine hydrochloride that had formed (abt. 4 g) was removed and the filtrate, washed with water up to neutrality, was concentrated to a constant weight yielding 17.2 g of technical product. This latter, purified by passing it on a silica gel column gave 7.5 g of O-ethyl-O-(2,4,5-trichlorophenyl)N3,3-dichloro-amido-thiophosphate.

Elementary analysis

Theoretical: C = 30.76%; H = 2.58%; N = 3.26%; P = 7.21%; Cl = 41.27%
Found values: C = 31.67%; H = 2.67%; N = 3.28%; P = 7.55%; Cl = 39.29%.
N.M.R. spectrum: in accordance with the structure indicated.
I.R. Spectrum: in agreement with the structure indicated.

EXAMPLES 2 TO 18

Following the same procedures as those described in the previous example, starting from suitable reactants and by letting the condensation reaction between arylphosphorothiodichloride and alcohol take place at temperatures comprised between −30° C and +30° C, followed up by the condensation of the product thus obtained with amine, there were prepared and isolated the following compounds showing the elementary compositions reported below:

EXAMPLE 2

O-ethyl-O-(2,4-dichlorophenyl)N-3,3,-dichloroallylamido-thiophosphate:
theoretical: C = 33.44%;
found: C = 34.94%;
theoretical: H = 3.06%;
found: H = 3.38%;
theoretical: Cl = 35.90%;
found: Cl = 35.43%;
theoretical: S = 8.12%;
found: S = 7.89%;

EXAMPLE 3

O-ethyl-O(3-methyl-4nitrophenyl)N-3,3-dichloroallylamido-thiophosphate:
theoretical: C = 37.42%;
found: C = 37.90%;
theoretical: H = 3.90%;
found: H = 4.00%;
theoretical: Cl = 18.45%;
found: Cl = 18.10%;
theoretical: S = 8.32%;
found: S = 7.95%;

EXAMPLE 4

O-methyl-O-(3-methyl-4-methylthiophenyl)-N-methyl-N-3,3-dichloroallylamido-thiophosphate:
theoretical: C = 40.40%;
found: C = 40.9%;
theoretical: H = 4.66%;
found: H = 4.8%;
theoretical: Cl = 18.35%;
found: Cl = 17.8%;
theoretical: S = 16.55%;
found: S = 17.1%;

EXAMPLE 5

O-methyl-O-(2,5dichloro-4-bromophenyl)-N-2,3,3-trichloroallylamido-thiophosphate:
theoretical: C = 24.30%;
found: C = 24.70%;
theoretical: H = 1.60%;

found: H = 1.80%;
theoretical: Cl = 35.85%;
found: Cl = 35.40%;
theoretical: S = 6.45%;
found: S = 6.9%;

| EXAMPLE | CHARACTERISTICS | THEORETICAL | FOUND |
|---|---|---|---|
| 6 | O-ethyl-O-(3-methyl-4-nitro-phenyl)-N-(3,3-dichloro-allyl-amido-thio-phosphate | Cl = 18,41 %<br>P = 8,04 % | 16,6 %<br>7,25 % |
| 7 | O-iso-propyl-O-(2,4,5-trichloro-phenyl)-N-(3,3-dichloro-allyl-amido-thio-phosphate | Cl = 39,97 %<br>S = 7,23 % | 39,84 %<br>7,12 % |
| 8 | O-methyl-O-(2,4,5-trichloro-phenyl)-N-(3,3-dichloro-allyl)-amido-thio-phosphate | Cl = 42,67 %<br>S = 7,72 % | 39,88 %<br>7,25 % |
| 9 | O-methyl-O-(p-nitro-phenyl)-N-(3,3-dichloro-allyl)-amido-thio-phosphate | Cl = 19,85 %<br>P = 8,67 %<br>S = 8,98 % | 21,27 %<br>11,02 %<br>9,16 % |
| 10 | O-methyl-O-(3-methyl-4-nitro-phenyl)-N-(3,3-dichloro-allyl)-amido-thio-phosphate | Cl = 19,11 %<br>P = 8,35 %<br>S = 8,64 % | 21,96 %<br>9,21 %<br>10,00 % |
| 11 | O-methyl-O-(3-methyl-4-methyl-thio-phenyl)-N-(3,3-dichloro-allyl)-amido-thio-phosphate | Cl = 19,05 %<br>P = 8,32 %<br>S = 17,23 % | 19,92 %<br>7,95 %<br>15,88 % |
| 12 | O-ethyl-O-(3-methyl-4-methyl-thio-phenyl)-N-(3,3-dichloro-allyl)-amido-thio-phosphate | Cl = 18,36 %<br>P = 8,02 %<br>S = 16,60 % | 22,81 %<br>9,39 %<br>14,13 % |
| 13 | O-iso-propyl-O-(3-methyl-4-methyl-thio-phenyl)-N-(3,3-dichloro allyl)-amido-thio-phosphate | Cl = 17,71 %<br>P = 7,74 %<br>S = 16,02 % | 22,81 %<br>9,78 %<br>13,06 % |
| 14 | O-methyl-O-(3-methyl-4-methyl-thio-phenyl)-N-methyl-N-(3,3-dicloro-allyl-amido-thio-phospate | Cl = 18,34 %<br>P = 8,01 %<br>S = 16,59 % | 24,52 %<br>7,74 %<br>14,00 % |
| 15 | O-ethyl-O-(3-methyl-4-methyl-thio-phenyl)-N-methyl-N-(3,3-dicloro-allyl)-amido-thio-phosphate | Cl = 17,71 %<br>P = 7,74 %<br>S = 16,02 % | 17,38 %<br>8,24 %<br>13,61 % |
| 16 | O-iso-propyl-O-(3-methyl-4-methyl-thio-phenyl)-N-methyl-N-(3,3-dichloro-allyl)-amido-thio-phosphate | Cl = 17,11 %<br>P = 7,48 %<br>S = 15,48 % | 16,51 %<br>7,50 %<br>15,54 % |
| 17 | O-ethyl-O-(p-nitro-phenyl)-N-(3,3-dichloro-allyl)-amido-thio-phosphate | Cl = 19,10 %<br>P = 8,35 %<br>S = 8,64 | 21,34 %<br>8,44 %<br>7,33% |
| 18 | O-ethyl-O-(p-nitro-phenyl9-N-methyl-N-(3,3-dicloro-allyl)-amido-thio-phosphate | Cl = 19,41 %<br>P = 8,04 %<br>S = 8,32 % | 18,16 %<br>7,86 %<br>7,65 % |

NMR spectra and I.R. spectra in agreement with the indicated formulae.

EXAMPLE 19

Activity tests on *Macrosiphum cuphorbiac* (aphides).

Small potato plants, grown in pots, were infested with adult aphide females and, after a few hours, subjected to besprinkling with an aqueous dispersion of the product of Example 1, at a concentration of 0.1%. The percentual death-rate turned out to be 100% (on small untreated plants = 0).

EXAMPLE 20

Activity test on *Culex pipiens* (Diptera).

Into glasses containing an aqueous dispersion of the product of Example 1 and at a concentration of 0.005 parts per million, p.p.m.: there were introduced larvae of third and fourth age. The death-rate proved to be 100% at that concentration, after 24 hours from the treatment (in the glasses containing pure water, the death-rate equalled 0).

EXAMPLE 21

Activity test on *Leptinotarsa decemlineata* (Coleopters).

Potato plants grown in pots were infested with 4-day old larvae and subjected to besprinkling with an aqueous 0.1% dispersion of the product of Example 1.

The percentual death-rate of the larvae after 48 hrs from the treatment proved to be 100% (on the untreated plants the death-rate turned out to be equal to 0).

EXAMPLE 22

Activity test on *Musca domestica* or House-fly (Dipters).

Adult 4-day flies were treated by topical application by means of a micro-syringe of 1 cubic millimeters ($mm^3$) of an acetone solution at 0.5 $\gamma$/ $.mm^3$ according to Example 1. The death-rate after 24 hours proved to be 100%. (The death-rate of the flies treated with 1 $.mm^3$ of acetone under the same conditions was equal to 0).

EXAMPLE 23

In order to show how the compounds of the invention have different activities depending on the species at varying concentrations, the death-rate percentages on various infesting kinds of compounds of the invention at varying concentrations of active principle have been recorded in Table II.

TABLE II

Activity of some compounds of the invention at scalar concentrations (in %) on various infesting species.

| Reference No. | Anticholesterase Activity Structural Formula | Macrosiphum % a.p. | Euphorbiae % mort. | Pieris Brassicae % a.p. | % mort. | Leptinot. Decemlin. % a.p. | % mort. | Culex Pipens ppm a.p. | % mort. | Tetran. Urt. adults % a.p. | % mort. | Tetran Urt. eggs % a.p. | % mort. | Spodopt. Littoralis % a.p. | % mort. |
|---|---|---|---|---|---|---|---|---|---|---|---|---|---|---|---|
| M 6986 | $1,17 \cdot 10^{-6}$ $C_2H_5O$-P(=S)-O-C₆H₃(CH₃)(NO₂); Cl₂C=CH—CH₂—HN | 1 0,1 0,01 | 100 88 35 | 1 | 100 | 1 | 40 | 2 0,2 0,02 | 100 100 0 | 1 | 26 | 1 | 12 | 1 | 5 |
| M 7147 | $1,80 \cdot 10^{-5}$ (CH₃CHO-CH₃)-P(=S)-O-C₆H₂Cl₃; Cl₂C=CH—CH₂—HN | 1 0,1 0,01 | 99 65 17 | 1 | 20 | 1 | 75 | 2 0,2 0,02 | 100 98 5 | 1 | 47 | 1 | 12 | 1 | |
| M 7160 | $3,82 \cdot 10^{-6}$ CH₃O-P(=S)-O-C₆H₂Cl₃; Cl₂C=CH—CH₂—HN | 1 0,1 0,01 | 100 72 7 | 1 0,1 | 100 0 | 1 | 40 | 2 0,2 0,02 | 100 97 5 | 1 0,1 | 100 33 | 1 0,1 | 100 10 | 1 | 55 |
| M 7470 | CH₃-C₆H₃(SCH₃); C₂H₅O-P(=S)-O-; Cl₂C=CH—CH₂—N—CH₃ | 1 0,1 0,01 | 100 84 8 | 1 0,1 | 100 0 | 1 0,1 | 75 0 | 2 0,2 0,02 0,005 | 100 100 100 0 | 1 0,1 0,01 | 100 49 0 | 1 0,1 | 100 13 | 1 | 25 |
| M 7471 | CH₃-C₆H₃(SCH₃); iso C₃H₇O-P(=S)-O-; Cl₂C=CH—CH₂—N—CH₃ | 1 0,1 | 70 18 | 1 0,1 | 77 0 | 1 | 65 | 2 0,2 0,02 | 100 91 22 | 1 | 57 | 1 0,1 | 100 10 | 1 | 0 |
| M 7414 | CH₃O-P(=S)-O-C₆H₃(CH₃)(NO₂); Cl₂C=CH—CH₂—HN | 1 0,1 0,01 | 100 85 6 | 1 0,1 | 80 5 | 1 0,1 | 80 0 | 2 0,2 0,02 | 100 100 0 | 1 0,1 0,01 | 100 85 0 | 1 0,1 | 99 9 | 1 | |
| M 7415 | | | | | | | | | | | | | | | |

TABLE II-continued
Activity of some compounds of the invention at scalar concentrations (in %) on various infesting species.

| Reference No. | Structural Formula | Anticholesterase Activity % | Macrosiphum a.p. | Euphorbiae % mort. | Pieris Brassicae a.p. | % mort. | Leptinot. Decemlin. a.p. | % mort. | Oulex Pipens ppm a.p. | % mort. | Tetran. a.p. | % mort. | Urt. adults % mort. | Tetran % a.p. | Urt. eggs % mort. | Spodopt. a.p. | Littoralis % mort. |
|---|---|---|---|---|---|---|---|---|---|---|---|---|---|---|---|---|---|
| M 7466 | CH₃O\P(=S)\O-[C₆H₃(CH₃)(NO₂)]; Cl₂C=CH—CH₂—HN | 1 | 0,1 | 97 74 | 1 0,1 | 100 10 | 1 | 70 | 2 0,2 0,02 | 100 100 5 | 1 0,1 | 100 21 | 1 0,1 | 95 6 | | |
| M 7467 | CH₃O\P(=S)\O-[C₆H₃(CH₃)(SCH₃)]; Cl₂C=CH—CH₂—HN | 1 0,01 | 0,1 | 100 80 24 | 1 0,1 | 95 0 | 1 0,1 | 80 0 | 2 0,2 0,02 0,005 | 100 100 100 51 | 1 0,1 0,01 | 100 100 40 | 1 0,1 0,01 | 100 88 15 | 1 | 0 |
| M7468 | C₂H₅O\P(=S)\O-[C₆H₃(CH₃)(SCH₃)]; Cl₂C=CH—CH₂—HN | 1 | 0,1 | 90 54 | 1 0,1 | 87 35 | 1 | 55 | 2 0,2 0,02 0,005 | 100 100 100 39 | 1 0,1 0,01 | 100 100 0 | 1 0,1 | 100 58 | 1 | 30 |
| M7469 | iso C₃H₇O\P(=S)\O-[C₆H₃(CH₃)(SCH₃)]; Cl₂C=CH—CH₂—HN | 1 | 0,1 | 81 41 | 1 0,1 | 85 12 | 1 | 30 | 2 0,2 0,02 | 100 100 30 | 1 0,1 | 100 0 | 1 0,1 | 100 16 | 1 | 0 |
| | CH₃O\P(=S)\O-[C₆H₃(CH₃)(SCH₃)]; Cl₂C=CH—CH₂—N(CH₃) | 1 0,01 | 0,1 | 100 55 | 1 0,1 | 82 0 | 1 | 20 | 2 0,2 0,22 0,005 | 100 100 95 0 | 1 0,1 | 100 36 | 1 0,1 | 100 24 | 1 | 15 |

We claim:

1. An N-polychloroallylamido-thiophosphoric ester having the general formula:

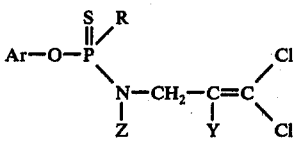

wherein:

Ar is phenyl substituted with from 1 to 3 halogen atoms and/or nitro, methyl or thiomethyl;

R is selected from among $CH_3O$, $C_2H_5O$, iso-$C_3H_7O$, phenyl and phenyl substituted with from 1 to 3 halogen atoms and/or nitro, methyl or thiomethyl;

Z is selected from among H,

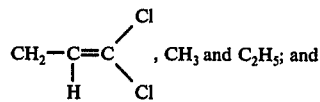

, $CH_3$ and $C_2H_5$; and y is selected from among H and Cl.

2. An ester according to claim 1, characterized in that it is O-ethyl-O-(2,4,5-trichlorophenyl)-N-(3,3-dichloroallyl)-amido-thiophosphate.

3. An ester according to claim 1, characterized in that it is O-ethyl-O-(2,4-dichlorophenyl)-N-3,3-dichloroallyl-amido-thiophosphate.

4. An ester according to claim 1, characterized in that it is O-ethyl-O-(3-methyl-4-nitrophenyl)-N-3,3-dichloroallylamido-thiophosphate.

5. An ester according to claim 1, characterized in that it is O-methyl-O-(3-methyl-4-methyl-thiophenyl)-N-methyl-N-3,3-dichloroallyl-amido-thiophosphate.

6. An ester according to claim 1, characterized in that it is O-methyl-O-(2,5-dichloro-4-bromophenyl)-N-2,3,3-trichloroallyl-amido-thiophosphate.

* * * * *